US006758853B2

(12) United States Patent
Kieturakis et al.

(10) Patent No.: US 6,758,853 B2
(45) Date of Patent: *Jul. 6, 2004

(54) APPARATUS AND METHODS FOR DEVELOPING AN ANATOMIC SPACE FOR LAPAROSCOPIC HERNIA REPAIR AND PATCH FOR USE THEREWITH

(75) Inventors: Maciej J. Kieturakis, San Carlos, CA (US); Kenneth H. Mollenauer, Santa Clara, CA (US); Michelle Y. Monfort, Los Gatos, CA (US)

(73) Assignee: General Surgical Innovations, Inc., Norwalk, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/076,771

(22) Filed: Feb. 13, 2002

(65) Prior Publication Data

US 2002/0107539 A1 Aug. 8, 2002

Related U.S. Application Data

(62) Division of application No. 09/932,156, filed on Aug. 17, 2001, now Pat. No. 6,565,590, which is a continuation of application No. 07/893,988, filed on Jun. 2, 1992, now Pat. No. 6,312,442.

(51) Int. Cl.[7] ............................................. A61B 17/00
(52) U.S. Cl. ...................... 606/190; 600/207; 128/898; 606/151
(58) Field of Search .......................... 606/151, 191–200, 606/213; 128/898; 600/201, 204, 207, 210; 604/96.01–109

(56) References Cited

U.S. PATENT DOCUMENTS 1,213,005 A    1/1917   Pillsbury
512,456 A      9/1939   Sadilkova
2,854,983 A    10/1958  Baskin
2,936,760 A    5/1960   Gants
3,039,468 A    6/1962   Price (List continued on next page.)

FOREIGN PATENT DOCUMENTS

| DE | 2157727        | 8/1973  |
|----|----------------|---------|
| EP | 512456         | 9/1939  |
| EP | 0573 273 A3    | 12/1993 |
| EP | 0573 273 B1    | 12/1993 |
| EP | 0573 273 A2    | 12/1993 |
| RU | 594960         | 2/1992  |
| WO | WO 92/06632 A1 | 4/1992  |
| WO | WP 92/06638 A1 | 4/1992  |

OTHER PUBLICATIONS

Berci, G. "Laparoscopy in General Surgery" in: Berci, G. Endoscopy (New York, Appleton–Century–Crofts, 1976), pp. 382–412.

(List continued on next page.)

*Primary Examiner*—Glenn K. Dawson

(57) ABSTRACT

Laparoscopic apparatus and method for insertion into a space or potential space in a body including an introducer device having a tubular member with a bore extending therethrough. A tunneling shaft assembly is provided and is slidably mounted in the bore of the introducer device. The tunneling shaft assembly includes a tunneling shaft having proximal and distal extremities. A tunneling member is mounted on the distal extremity of the tunneling shaft. A balloon assembly is provided which is removably secured to the tunneling shaft. The balloon assembly includes a balloon wrapped about said tunneling shaft. A sheath is provided which encloses the balloon on the tunneling shaft. The sheath has a slit extending longitudinally thereof permitting the sheath to be removed whereby the balloon can be released and inflated. A tubular member is provided which has a balloon inflation lumen thereon and is coupled to the balloon for inflating said balloon.

5 Claims, 12 Drawing Sheets

U.S. PATENT DOCUMENTS

| | | |
|---|---|---|
| 3,253,594 A | 5/1966 | Matthews et al. |
| 3,417,745 A | 12/1968 | Sheldon |
| 3,459,175 A | 8/1969 | Miller |
| 3,545,443 A | 12/1970 | Ansari |
| 3,774,596 A | 11/1973 | Cook |
| 3,800,788 A | 4/1974 | White |
| 3,882,852 A | 5/1975 | Sinnreich |
| 3,915,171 A | 10/1975 | Shermeta |
| RE29,207 E | 5/1977 | Bolduc et al. |
| 4,077,412 A | 3/1978 | Moossun |
| 4,083,369 A | 4/1978 | Sinnreich |
| 4,177,814 A | 12/1979 | Knepshield et al. |
| 4,198,981 A | 4/1980 | Sinnreich |
| 4,217,889 A | 8/1980 | Radovan et al. |
| 4,243,050 A | 1/1981 | Littleford |
| 4,276,874 A | 7/1981 | Wolvek et al. |
| 4,312,353 A | 1/1982 | Shabbabian |
| 4,345,606 A | 8/1982 | Littleford |
| 4,411,654 A | 10/1983 | Boarini |
| 4,490,137 A | 12/1984 | Moukheibir |
| 4,496,345 A | 1/1985 | Hasson |
| 4,501,266 A | 2/1985 | McDaniel |
| 4,555,242 A | 11/1985 | Saudagar |
| 4,574,806 A | 3/1986 | McCarthy |
| 4,581,025 A | 4/1986 | Timmermans |
| 4,589,868 A | 5/1986 | Dretler |
| 4,593,682 A | 6/1986 | Heckele |
| 4,596,554 A | 6/1986 | Dastgeer |
| 4,596,559 A | 6/1986 | Fleischhacker |
| 4,610,662 A | 9/1986 | Weikl et al. |
| 4,644,936 A | 2/1987 | Schiff |
| 4,651,717 A | 3/1987 | Jakubezak |
| 4,654,030 A | 3/1987 | Moll et al. |
| 4,685,447 A | 8/1987 | Iversen et al. |
| 4,706,670 A | 11/1987 | Andersen et al. |
| 4,738,666 A | 4/1988 | Fuqua |
| 4,754,030 A | 6/1988 | Kaplan et al. |
| 4,769,038 A | 9/1988 | Bendavid et al. |
| 4,772,266 A | 9/1988 | Groshong |
| 4,779,611 A | 10/1988 | Grooters et al. |
| 4,784,133 A | 11/1988 | Mackin |
| 4,793,348 A | 12/1988 | Palmaz |
| 4,798,205 A | 1/1989 | Bonomo et al. |
| 4,800,901 A | 1/1989 | Rosenberg |
| 4,802,479 A | 2/1989 | Haber et al. |
| 4,813,429 A | 3/1989 | Eshel et al. |
| 4,840,613 A | 6/1989 | Balbierz |
| 4,854,316 A | 8/1989 | Davis |
| 4,861,334 A | 8/1989 | Hawaz |
| 4,865,593 A | 9/1989 | Ogawa et al. |
| 4,869,717 A | 9/1989 | Adair |
| 4,875,468 A | 10/1989 | Krauter et al. |
| 4,888,000 A | 12/1989 | McQuilkin et al. |
| 4,899,729 A | 2/1990 | Gill et al. |
| 4,917,668 A | 4/1990 | Haindl |
| 4,927,412 A | 5/1990 | Menasche |
| 4,931,042 A | 6/1990 | Holmes et al. |
| 4,932,956 A | 6/1990 | Reddy et al. |
| 4,955,895 A | 9/1990 | Sugiyama et al. |
| 4,966,583 A | 10/1990 | Debbas |
| 4,994,047 A | 2/1991 | Walker et al. |
| 5,002,557 A | 3/1991 | Hasson |
| 5,009,643 A | 4/1991 | Reich et al. |
| 5,030,206 A | 7/1991 | Lander |
| 5,030,227 A | 7/1991 | Rosenbluth et al. |
| 5,042,976 A | 8/1991 | Ishitsu et al. |
| 5,074,871 A | 12/1991 | Groshong |
| 5,098,392 A | 3/1992 | Fleischhacker et al. |
| 5,104,383 A | 4/1992 | Shichman |
| 5,116,318 A | 5/1992 | Hillstead |
| 5,116,357 A | 5/1992 | Eberbach |
| 5,122,122 A | 6/1992 | Allgood |
| 5,122,155 A | 6/1992 | Eberbach |
| 5,137,512 A | 8/1992 | Burns et al. |
| 5,141,494 A | 8/1992 | Danforth et al. |
| 5,141,515 A | 8/1992 | Eberbach |
| 5,147,302 A | 9/1992 | Euteneuer et al. |
| 5,147,316 A | 9/1992 | Castillenti |
| 5,147,374 A | 9/1992 | Fernandez |
| 5,152,278 A | 10/1992 | Clayman |
| 5,158,545 A | 10/1992 | Trudell et al. |
| 5,159,925 A | 11/1992 | Neuwirth et al. |
| 5,163,949 A | 11/1992 | Bonutti |
| 5,176,128 A | 1/1993 | Andrese |
| 5,176,649 A | 1/1993 | Wakabayashi |
| 5,176,692 A | 1/1993 | Wilk et al. |
| 5,183,463 A | 2/1993 | Debbas |
| 5,183,465 A | 2/1993 | Xanthakos et al. |
| 5,188,596 A | 2/1993 | Condon et al. |
| 5,188,630 A | 2/1993 | Christoudias |
| 5,190,541 A | 3/1993 | Abele et al. |
| 5,195,506 A | 3/1993 | Hulfish |
| 5,195,507 A | 3/1993 | Bilweis |
| 5,197,971 A | 3/1993 | Bonutti |
| 5,201,742 A | 4/1993 | Hasson |
| 5,201,752 A | 4/1993 | Brown et al. |
| 5,201,754 A | 4/1993 | Crittenden et al. |
| 5,209,725 A | 5/1993 | Roth |
| 5,215,526 A | 6/1993 | Deniega et al. |
| 5,220,928 A | 6/1993 | Oddsen et al. |
| 5,222,970 A | 6/1993 | Reeves |
| 5,226,429 A | 7/1993 | Kuzmak |
| 5,226,890 A | 7/1993 | Ianniruberto et al. |
| 5,232,446 A | 8/1993 | Arney |
| 5,258,026 A | 11/1993 | Johnson et al. |
| 5,261,888 A | 11/1993 | Semm |
| 5,267,965 A | 12/1993 | Deniega |
| 5,269,753 A | 12/1993 | Wilk |
| 5,284,474 A | 2/1994 | Adair |
| 5,290,249 A | 3/1994 | Foster et al. |
| 5,295,994 A | 3/1994 | Bonutti |
| 5,308,327 A | 5/1994 | Heaven et al. |
| 5,309,896 A | 5/1994 | Moll et al. |
| 5,314,443 A | 5/1994 | Rudnick |
| 5,318,012 A | 6/1994 | Wilk |
| 5,330,497 A | 7/1994 | Freitas et al. |
| 5,331,975 A | 7/1994 | Bonutti |
| 5,338,305 A | 8/1994 | Plyley et al. |
| 5,342,307 A | 8/1994 | Euteneuer et al. |
| 5,346,504 A | 9/1994 | Ortiz et al. |
| 5,359,995 A | 11/1994 | Sewell et al. |
| 5,361,752 A | 11/1994 | Moll et al. |
| 5,370,134 A | 12/1994 | Chin et al. |
| 5,383,889 A | 1/1995 | Warner et al. |
| 5,391,178 A | 2/1995 | Yapor |
| 5,397,311 A | 3/1995 | Walker et al. |
| 5,402,772 A | 4/1995 | Moll et al. |
| 5,407,433 A | 4/1995 | Loomas |
| 5,425,357 A | 6/1995 | Moll et al. |
| 5,431,173 A | 7/1995 | Chin et al. |
| 5,450,843 A | 9/1995 | Moll et al. |
| 5,454,365 A | 10/1995 | Bonutti |
| 5,496,345 A * | 3/1996 | Kieturakis et al. .......... 606/192 |
| 5,514,091 A | 5/1996 | Yoon |
| 5,607,443 A | 3/1997 | Kieturakis et al. |
| 5,707,382 A * | 1/1998 | Sierocuk et al. ............ 606/190 |
| 5,755,693 A | 5/1998 | Walker et al. |
| 5,836,961 A | 11/1998 | Kieturakis et al. |
| 6,312,442 B1 * | 11/2001 | Kieturakis et al. .......... 606/190 |

OTHER PUBLICATIONS

Cinelli, Rafael, M.D., "The Inflatable Silastic Bag: A Practical Devices that Simplifies Augmentation Mammaplasty," from the Division of Plastic Surgery, Department of Surgery, at the Maimonides Medical Center and Medical Arts Center of New York.

Dulucq, J.L. Treatment of Inguinal Hernias by Installation of a Subperitoneal Prosthetic Patch Using Pre–Peritoneoscopy (With a Video Film), Translation of French document from Chirugie, 1992, pp 118.

Ferzli et al, "Extraperitoneal Endoscopic Pelvic LympNode Dissection", J. Laparoendoscopic Surgery (1992), vol. 1, pp 39–44.

Gazayerli, M.M. "The Gazayerli Endoscopic Retractor Model 1" Surgeons Laparoscopy & Endoscopy (1991) vol. 1, pp. 98–100.

Gunning, J.E. "Chapter 2: History of Laparoscopy" in: Phillips, J.M. Laparoscopy (Baltimore, Maryland, Williams & Wilkins Company, 1977), pp. 6–14.

Haykawa, N. et al. "Laparoscopic Cholecystectomy Using Retraction of the Falciform Ligament", Surgical Caparoscopy & Endoscopy, vol. 1, No. 2, 1991, pp 126.

Hodgson, C. "Some Effects of the Peritoneal Insufflation of Carbon Dioxide of Laparoscopy", Anaesthesia, vol. 25, No. 3, Jul., 1970, pp 382–390.

Hoffman, M.D. Henry T. et al., "Nasal Reconstruction with the Rapidly Expanded Forehead Flap", Laryngoscope, 99:1096–1098, Oct. 1989.

Kaplan, L.R., et al. "Retroperitoneoscopy in dogs" Gastrointestinal Endoscopy (1979) vol. 25, No. 1, pp. 13–15.

Manders, M.D., Ernest K., Expert Report executed Dec. 1, 1997.

Marshall, R. L. "Circulatory Effects of Carbon Dioxide Insufflation of the Peritoneal Cavity for Laparoscopy", Brit. J. Anaesth. (1972), 44, pp 681–684.

Maxwell, "Immediate Intraoperative Expansion in Augmentation Mammoplasty", D18214, videotape.

Meretyk, S. et al. "Retroperitoneoscopy: Foreign Body Retrieval", The Journal of Urology, vol. 147, Jun., 1992, pp 1608–1611.

Rigg, M.D., Bruce M., "Inflatable Device for Intraoperative Use During Augmentation Mamaplasty", Reconstructive Surgery, May 1982.

Sanchez de Badajoz Chammorro et al., "Endoscopic Cervical Anchorage, New Treatment for Stress Incontinence", Archivos Españioles de Urologia: vol. 41, Issue 2, (1988), pp 127–130.

Sanchez de Badajoz Chammorro et al., "Stress Incontinence: A New Endoscopic Approach", Urology, vol. 36, No. 5, Nov., 1990, pp 403–405.

Sasaki, M.D., Gordon H., "Intraoperative Sustained Limited Expansion (ISLE) as an Immediate Reconstructive Technique", Clinics in Plastic Surgery, vol. 14, No. 3, Jul., 1987.

Sasaki, M.D., Gordon H., "Intraoperative Expansion™ as an Immediate Reconstructive Technique", Facial Plastic Surgery, 5:4, Jul., 1988.

Shafik, "Extraperitoneal Laparoscopic Lymphadenectomy in Prostatic Cancer: Preliminary Report of a New Approach", Journal of Endourology, vol. 6, No. 2, 1992, pp 113–116.

Voeller, M.D. Guy R., Expert Report executed Dec. 1, 1997.

Wickham, J.E.A. and Miller, R.A. Percutaneous Renal Surgery (New York, Churchill Livingstone, 1983), pp. 17–44.

Wittmoser, R. "Retroperitoneoscopy: A Preliminary Report" in: Berci, G. Endoscopy (New York, Appleton–Century–Crofts, 1976), pp. 760–761.

Zhila, V. "Surgical Interventions on the Kidneys and Ureters Using a Retroperitoneoscope", Translation of Russian Document from Urology Department of the Kiev State Institute for Physician Advancement of the USSR Ministry of Public Health.

Zucker, K.A., et al. Surgical Laparoscopy (St. Louis, Missouri, Quality Medical Publishing, Inc., 1991), pp. 25–26, pp. 313–317.

* cited by examiner

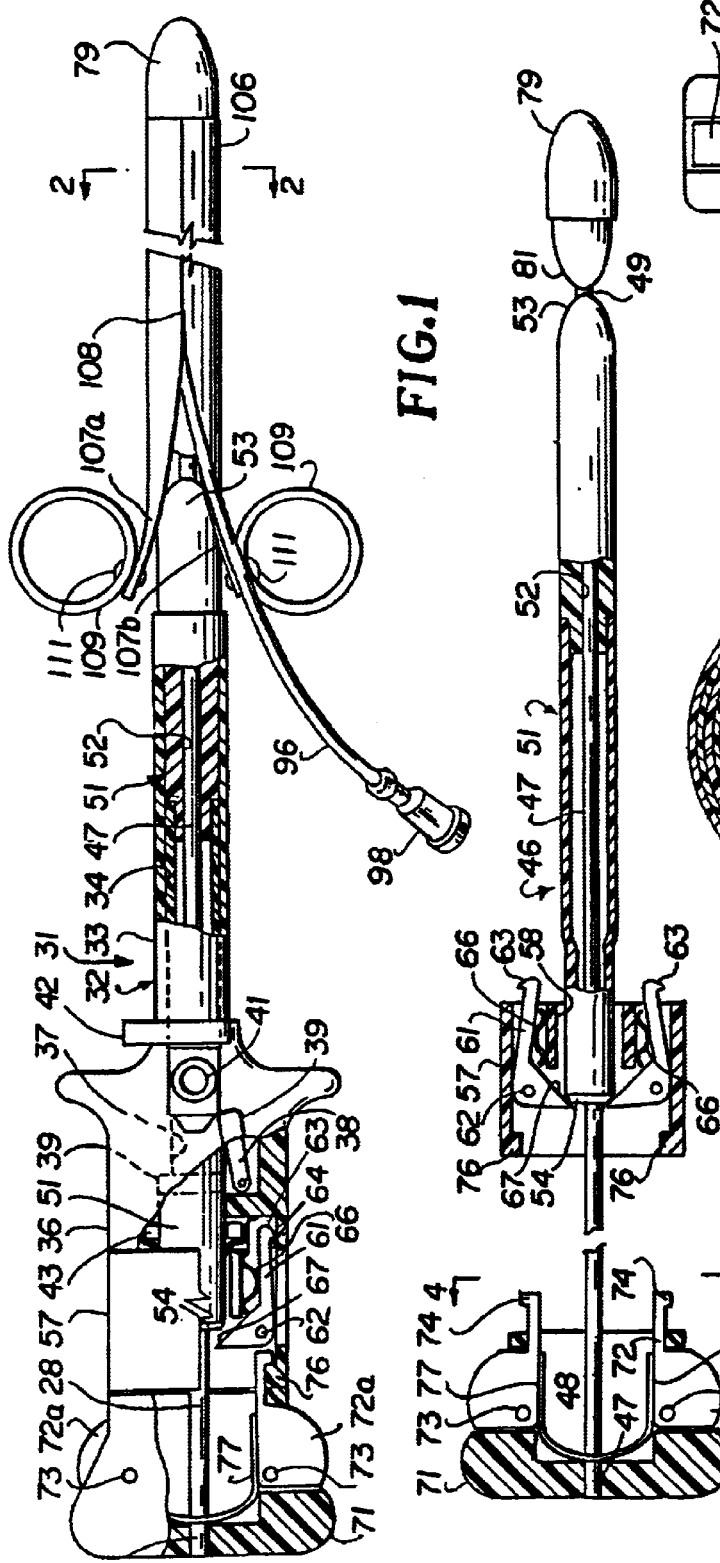
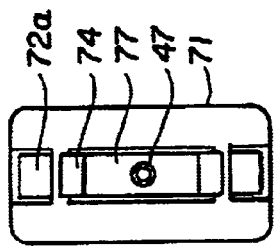
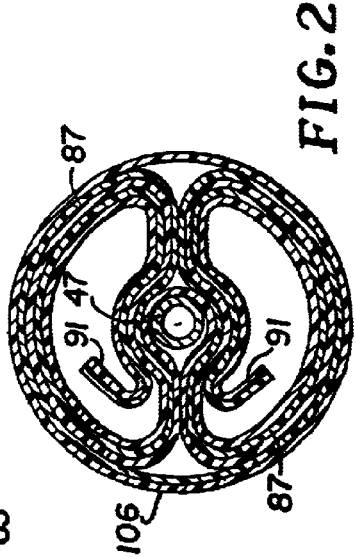
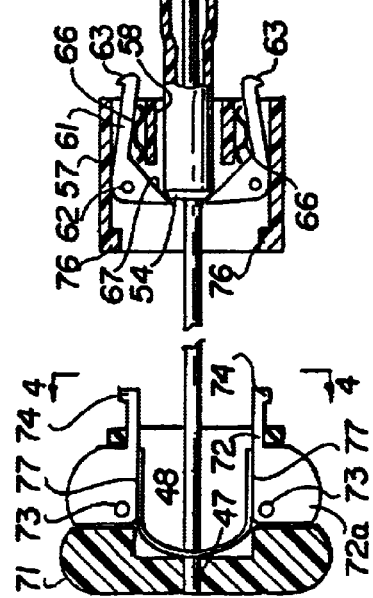
FIG. 1
FIG. 2
FIG. 3
FIG. 4

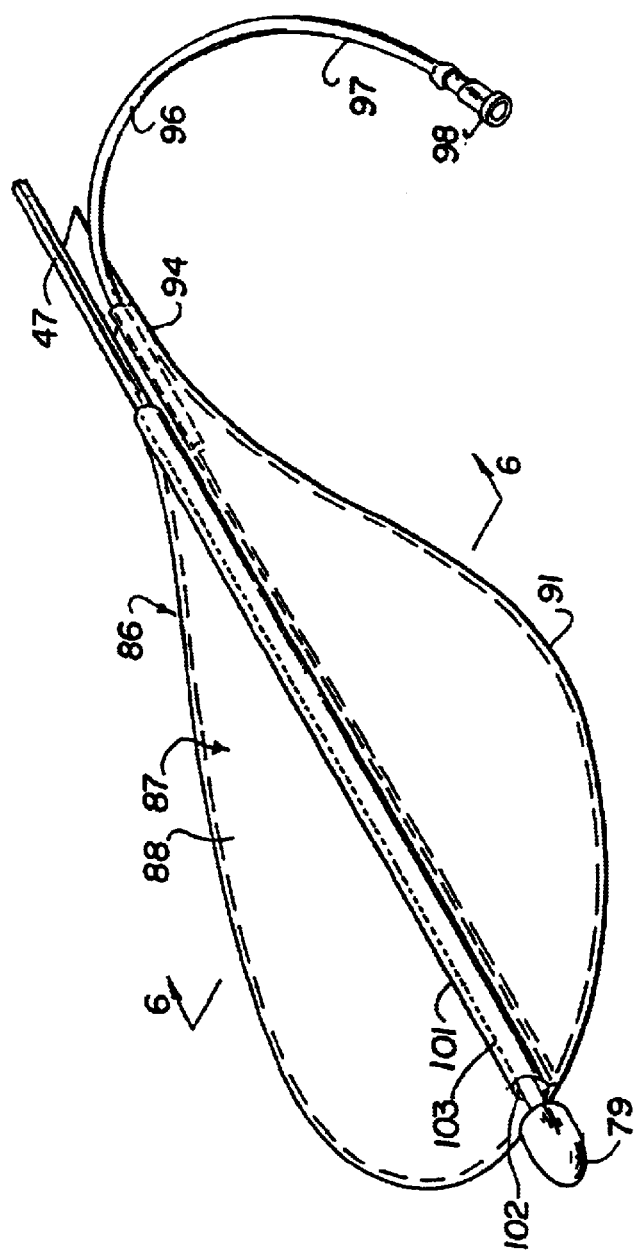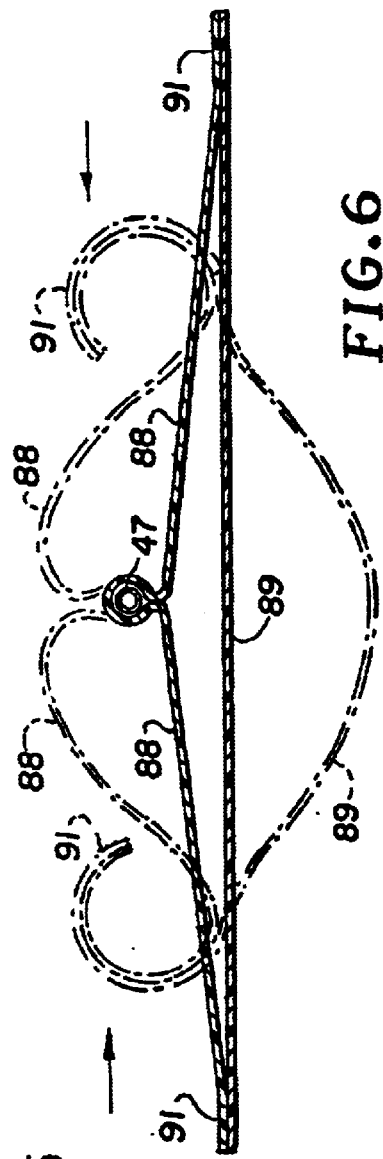

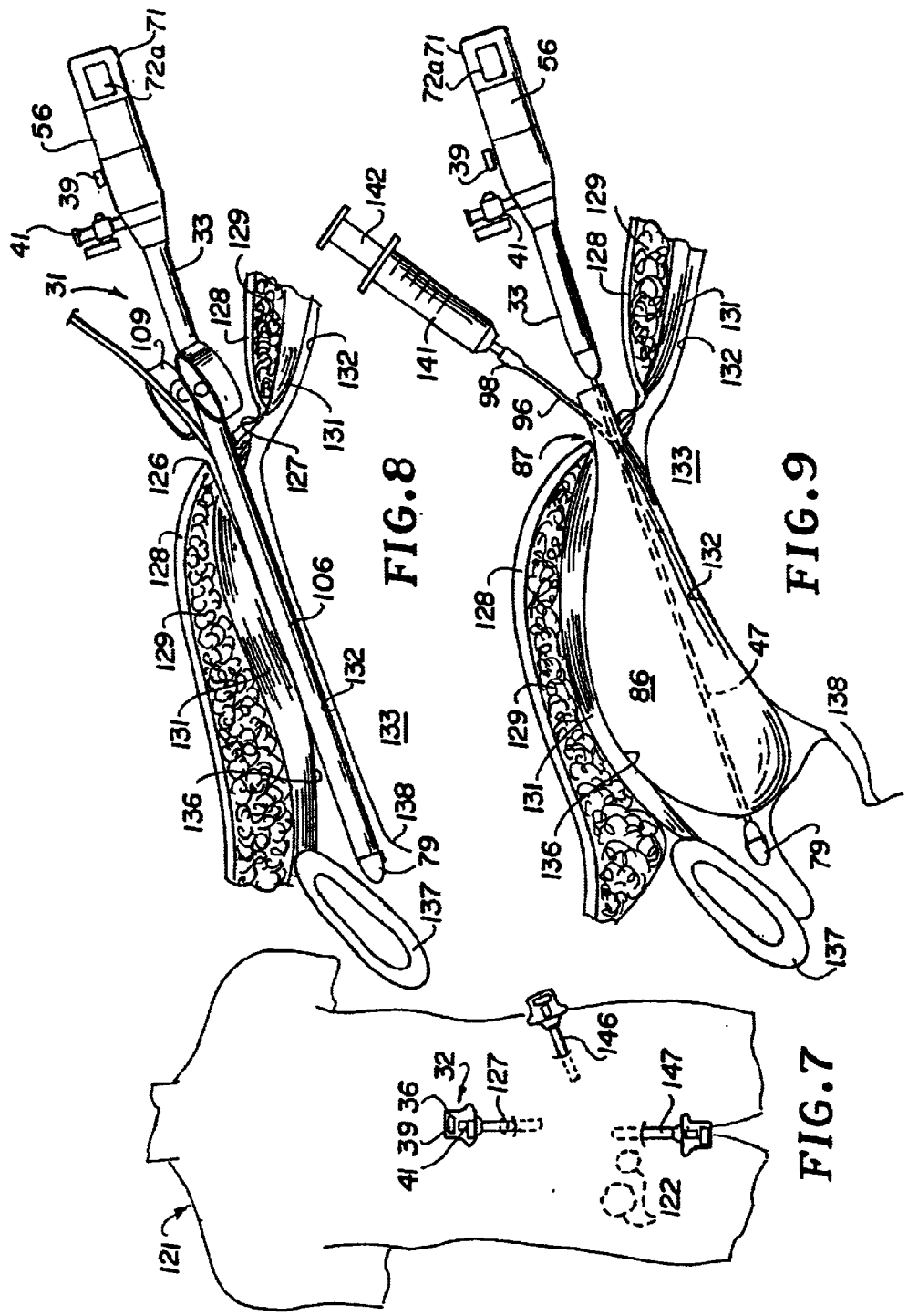

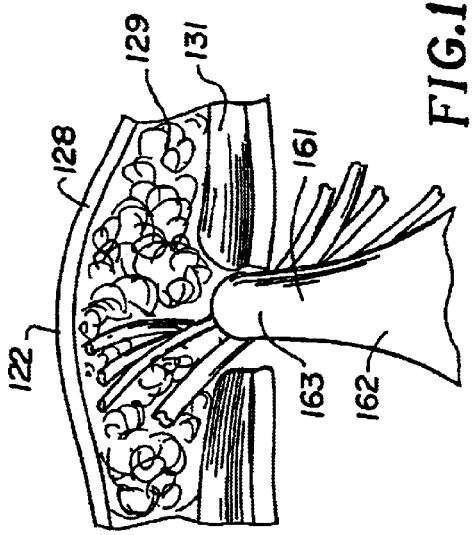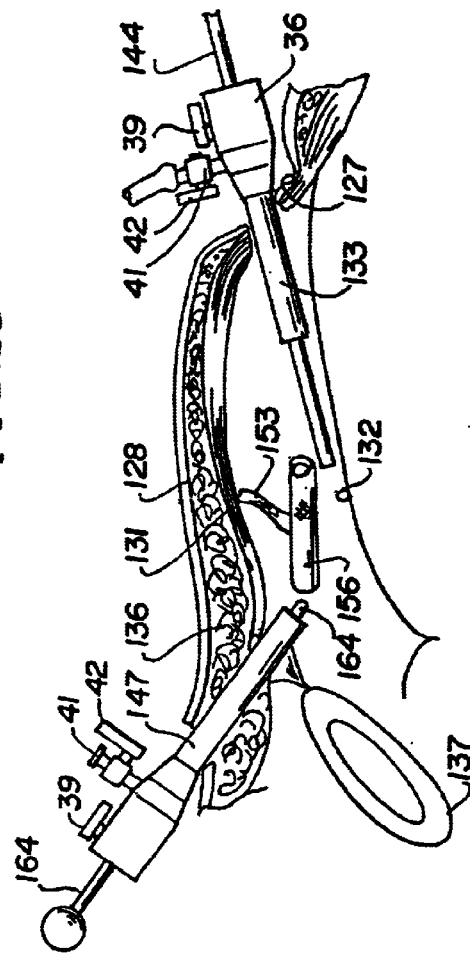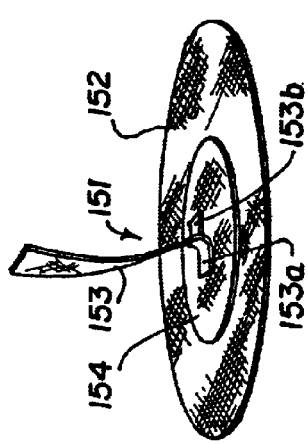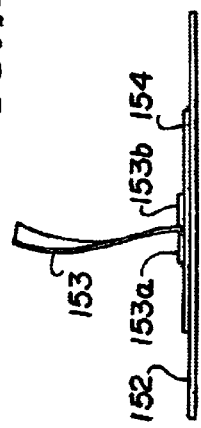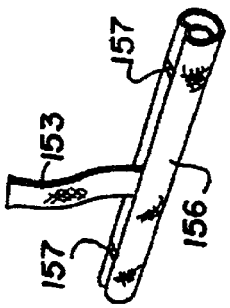

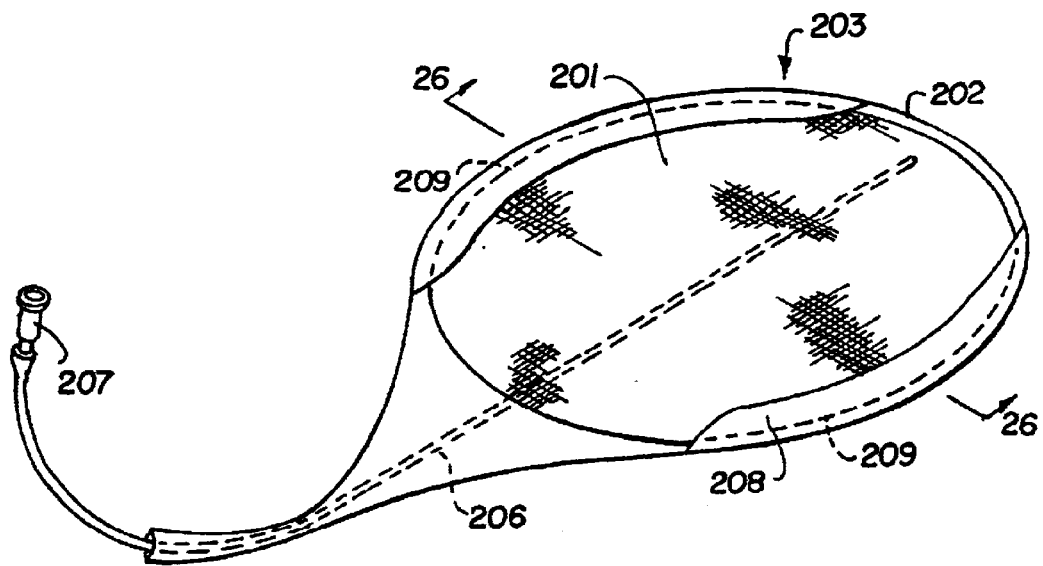
FIG. 25
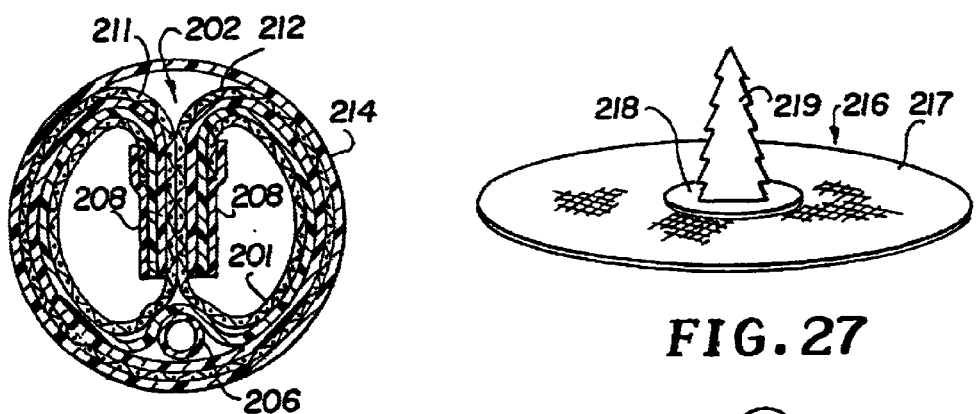
FIG. 26
FIG. 27
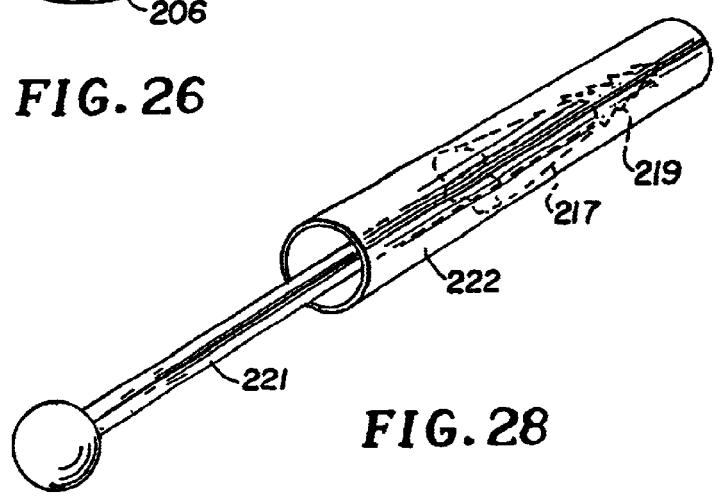
FIG. 28

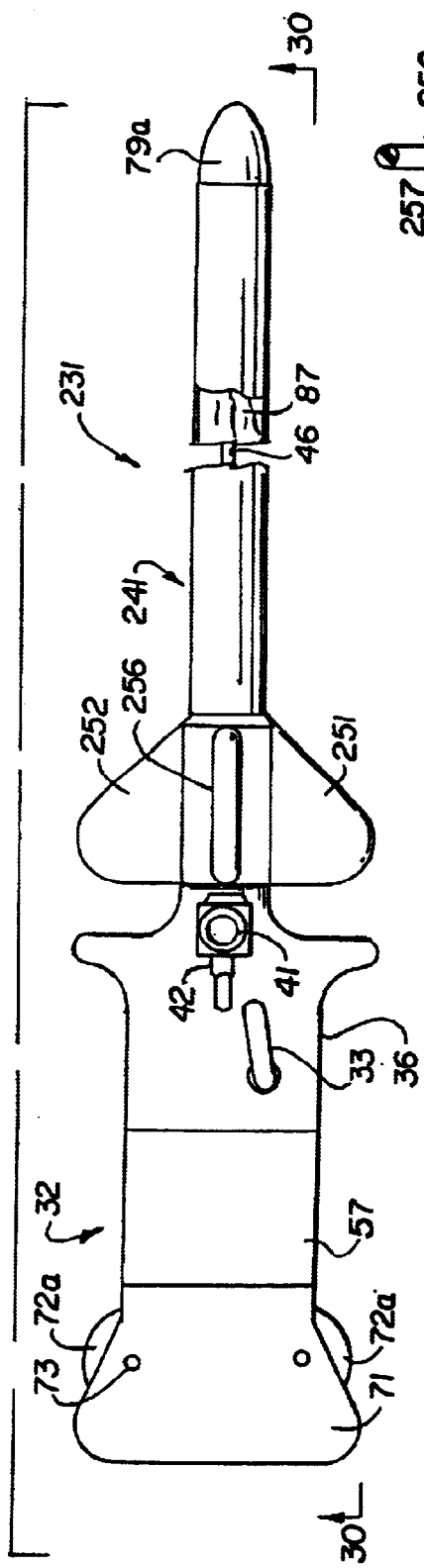
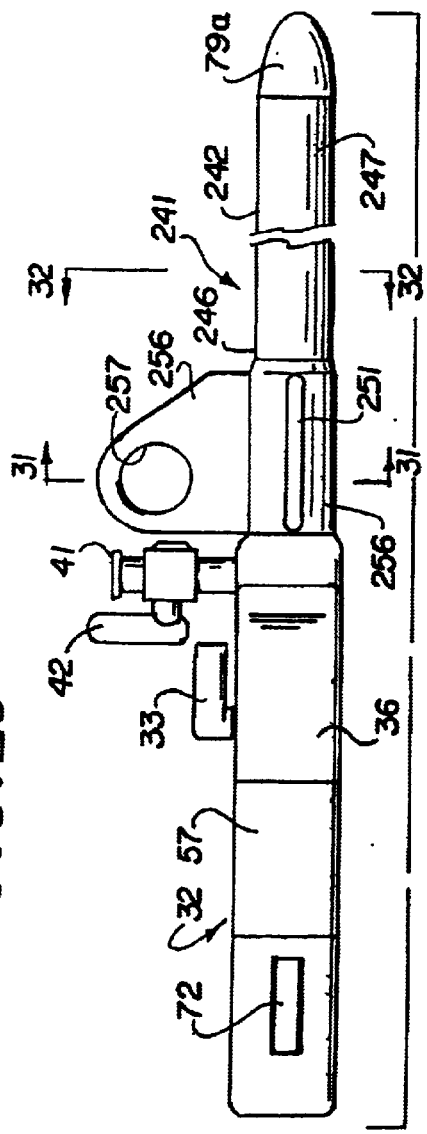
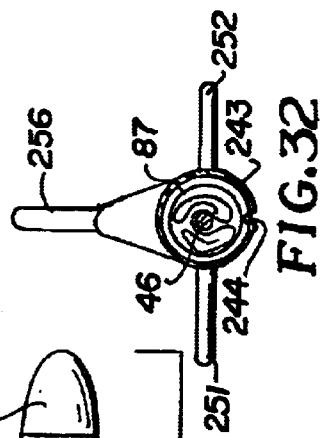
FIG.29
FIG.30
FIG.31
FIG.32

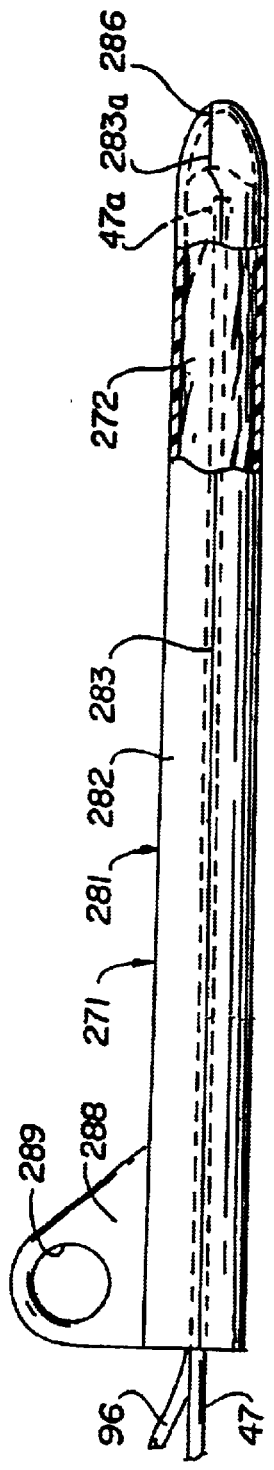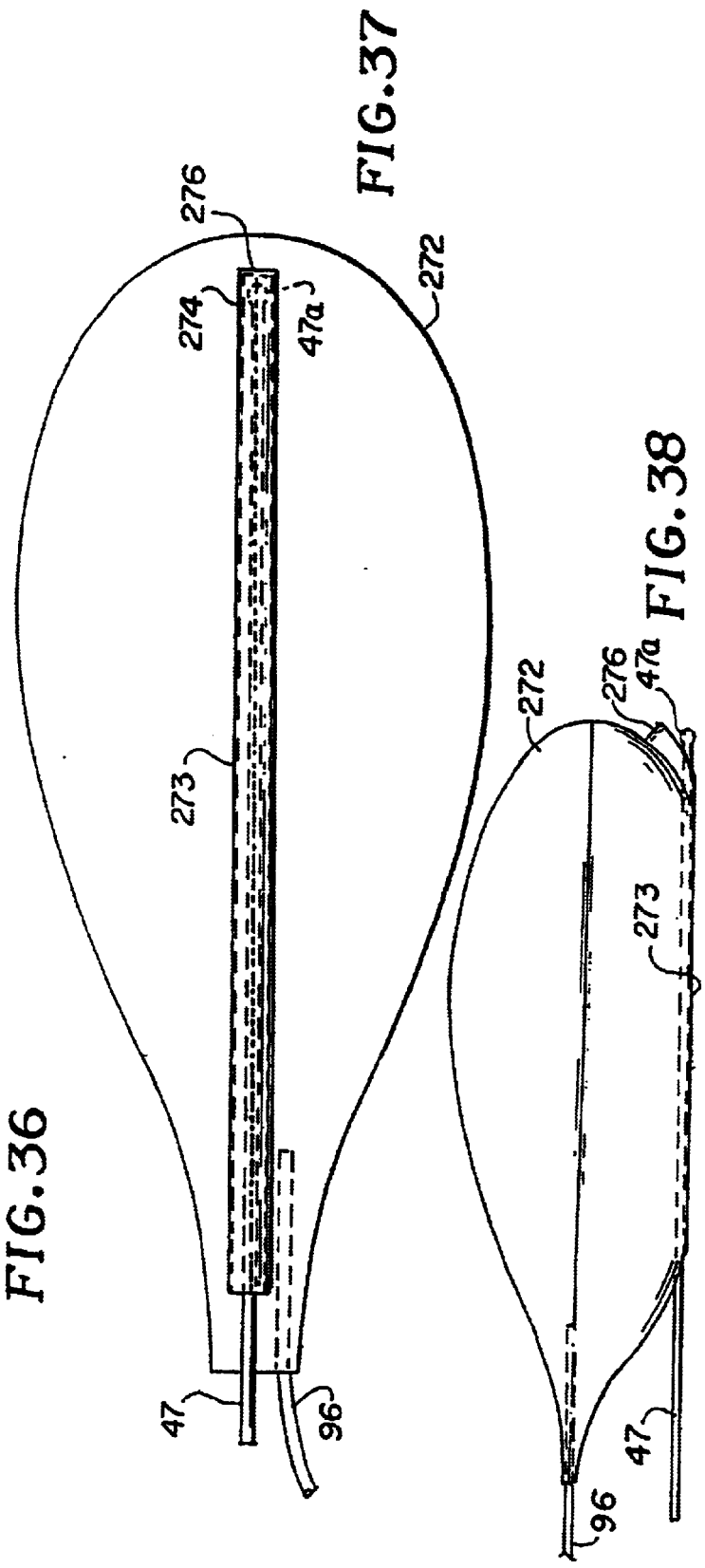

APPARATUS AND METHODS FOR DEVELOPING AN ANATOMIC SPACE FOR LAPAROSCOPIC HERNIA REPAIR AND PATCH FOR USE THEREWITH

CROSS-REFERENCE TO RELATED APPLICATIONS

This application is divisional of U.S. application Ser. No. 09/932,156, filed Aug. 17, 2001, now U.S. Pat. No. 6,565,590, which is a continuation of U.S. application Ser. No. 07/893,988, flied Jun. 2, 1992, now U.S. Pat. No. 6,312,442, the disclosures of which are hereby incorporated by reference in their entirety.

This invention relates to an apparatus and method for developing an anatomic space for laparoscopic hernia repair and a patch for use therewith.

In the past, in developing spaces and potential spaces within a body, blunt dissectors or soft-tipped dissectors have been utilized to create a dissected space which is parallel to the plane in which the dissectors are introduced into the body tissue. This often may be in an undesired plane, which can lead to bleeding which may obscure the field and make it difficult to identify the body structures. In utilizing such apparatus and methods, attempts have been made to develop anatomic spaces in the anterior, posterior or lateral to the peritoneum. The same is true for plural spaces and other anatomic spaces. Procedures that have been performed in such spaces include varocele dissection, lymph node dissection, sympathectomy and hernia repair. In the past, the inguinal hernia repair has principally been accomplished by the use of an open procedure which involves an incision in the groin to expose the defect in the inguinal floor, remove the hernial sac and subsequently suture the ligaments and fascias together to reinforce the weakness in the abdominal wall. Recently, laparoscopic hernia repairs have been attempted by inserting laparoscopic instruments into the abdominal cavity through the peritoneum and then placing a mesh to cover the hernia defect. Hernia repair using this procedure has a number of disadvantages, principally because the mesh used for hernia repair is in direct contact with the structures in the abdominal cavity, as for example the intestines, so that there is a tendency for adhesions to form in between these structures. Such adhesions are known to be responsible for certain occasionally serious complications. Such a procedure is also undesirable because typically the patch is stapled into the peritoneum, which is a very thin unstable layer covering the inner abdomen. Thus, the stapled patch can tear away from the peritoneum or shift its position. Other laparoscopic approaches involve cutting away the peritoneum and stapling it closed. This is time consuming and involves the risk of inadvertent cutting of important anatomic structures. In addition, such a procedure is undesirable because it requires the use of a general anesthesia. There is therefore a need for a new and improved apparatus and method for developing an anatomic space and particularly for accomplishing hernia repair by laparoscopy.

In general, it is an object of the present invention to provide an apparatus and method for developing an anatomic space.

Another object of the invention is to provide an apparatus and method in which such an anatomic space is developed by applying perpendicular forces to create the anatomic space at the weakest plane to create a more natural, less traumatic and bloodless region in which to work.

Another object of the invention is to provide an apparatus and method to obtain surgical exposure in the preperitoneal space.

Another object of the present invention is to provide an apparatus and method of the above character for developing an anatomic space for laparoscopic hernia repair through the anatomic space.

Another object of the invention is to provide an apparatus and method for decreasing the time and risk associated with creating a preperitoneal working space.

Another object of the present invention is to provide an apparatus and method of the above character for developing an anatomic space for laparoscopic hernia repair through the anatomic space.

Another object of the invention is to provide an apparatus and method of the above character which requires a minimally invasive procedure.

Another object of the invention is to provide an apparatus and method of the above character which can be accomplished without the use of a general anesthesia.

Another object of the invention is to provide an apparatus and method of the above character which can be accomplished with a spinal or epidural anesthesia.

Another object of the invention is to provide an apparatus and method of the above character which provides substantially reduced medical costs and a greatly reduced patient recovery time.

Another object of the invention is to provide an apparatus of the above character which is relatively simple and compact.

Another object of the invention is to provide an apparatus and method of the above character which can be readily utilized by surgeons.

Another object of the invention is to provide a patch for use in the apparatus which is firmly secured during the hernia repair.

Additional objects and features of the invention will appear from the following description in which the preferred embodiments are set forth in detail in conjunction with the accompanying drawings.

BRIEF DESCRIPTION OF THE DRAWINGS

FIG. 1 is a side elevational view partially in cross-section of a laparoscopic apparatus incorporating the present invention.

FIG. 2 is a cross-sectional view taken along the 2—2 of FIG. 1.

FIG. 3 is a side elevational view partially in cross-section of the tunneling shaft forming a part of the apparatus shown in FIG. 1 after it has been removed from the apparatus shown in FIG. 1.

FIG. 4 is a cross-sectional view taken along the line 4—4 of FIG. 3.

FIG. 5 is an isometric view of the inflatable balloon utilized in the apparatus in FIG. 1 secured to the tunneling rod.

FIG. 6 is a cross-sectional view taken along the line 6—6 of FIG. 5, and showing by dotted lines the manner in which the balloon as it unfolds develops the anatomic space.

FIG. 7 is a partial plan view of a prone human body, showing the lower abdomen showing the manner in which the laparoscopic apparatus of the present invention is utilized for performing a hernia repair through the preperitoneal space.

FIG. 8 is a sagittal view of the lower abdominal cavity of the human being shown in FIG. 7 showing the apparatus of the present invention introduced into the preperitoneal space.

FIG. 9 is a view similar to FIG. 8 but showing the sleeve removed from the apparatus and with the balloon inflated.

FIG. 12 is an isometric view of a patch incorporating the present invention.

FIG. 13 is a side elevational view of the patch shown in FIG. 12.

FIG. 14 is an isometric view showing the patch in FIGS. 12 and 13 in a rolled-up, generally cylindrical configuration.

FIG. 15 is a sagittal view showing the hernia sac of hernia that is to be repaired.

FIG. 16 is a sagittal view showing the introducer through which the rolled-up patch in FIG. 17 has been introduced into the preperitoneal space by an introducer rod.

FIG. 25 is an isometric view of another embodiment of a balloon and patch for use with the apparatus of the present invention.

FIG. 26 is a rolled-up cross-sectional view of the balloon and patch shown in FIG. 25.

FIG. 27 is an isometric view of another embodiment of a patch for use with the apparatus of the present invention.

FIG. 28 is an isometric view of the patch shown in FIG. 27 wrapped in an introducer assembly.

FIG. 29 is a top plan view of another embodiment of a laparoscopic apparatus incorporating the present invention.

FIG. 30 is a side elevational view taken along the line 30—30 of FIG. 29.

FIG. 31 is a cross-sectional view taken along the line 31—31 of FIG. 30.

FIG. 32 is a cross-sectional view taken along the line 32—32 of FIG. 30.

FIG. 36 is a side elevational view of another embodiment of a laparoscopic apparatus incorporating the present invention.

FIG. 37 is a plan view showing the balloon from the apparatus shown in FIG. 36 in an inflated condition and showing the tunneling rod mounted therein being prevented from being advanced beyond the distal extremity of the balloon.

FIG. 38 is a plan view showing the manner in which the balloon is separated from the tunneling rod as it is retracted.

Figure 10:
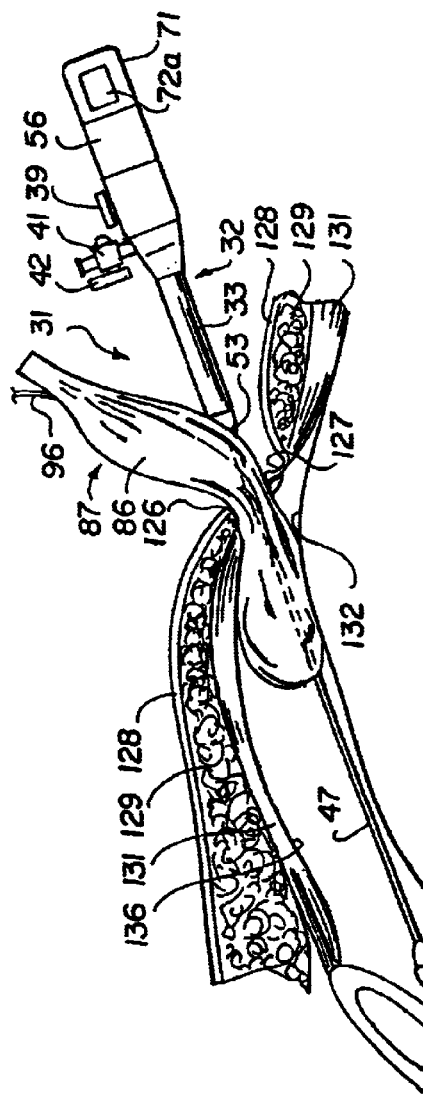
FIG. 10 is a sagittal view similar to FIG. 8 showing the balloon deflated and being removed.

In general, the apparatus of the present invention is used for insertion into a body to create an anatomic space. The apparatus is comprised of a tubular introducer member having a bore extending therethrough. A tunneling shaft is slidably mounted in the bore and has proximal and distal extremities including a bullet-shaped tip. A rounded tunneling member is mounted on the distal extremity of the tunneling shaft. An inflatable balloon is provided. Means is provided on the balloon for removably securing the balloon to the tunneling shaft. Means is also provided for forming a balloon inflation lumen for inflating the balloon. The balloon is wrapped on the tunneling shaft. A sleeve substantially encloses the balloon and is carried by the tunneling shaft. The sleeve is provided with a weakened region extending longitudinally thereof, permitting the sleeve to be removed whereby the balloon can be unwrapped and inflated so that it lies generally in a plane. The balloon as it is being inflated creates forces generally perpendicular to the plane of the balloon to cause pulling apart of the tissue along a natural plane to provide the anatomic space.

More in particular, as shown in the drawings, the apparatus or device 31 for creating such an anatomic space for use in a laparoscopic procedure (see FIG. 1) includes an introducer sleeve or device 32 which consists of a tubular member 33 formed of a suitable material such as plastic which is provided with a bore 34 extending throughout the length thereof. A handle section 36 is mounted on one end of the tubular member 33 and is also formed of a suitable material such as plastic. It is provided with a bore 37 which is in communication with the bore 33. A flapper valve 38 is mounted within the section 36 and is movable between a position in which it closes off the bore 37 and position out of the way of the bore 37, by means of a finger operated actuator 39 mounted on the exterior of the section 36. A stopcock 41 is mounted on the section 36 and is in communication with the passage 37. A lever 42 is provided for opening and closing the stopcock 41.

A tunneling shaft assembly 46 is slidably mounted in the bores 37 and 34 of the introducer sleeve 32. The tunneling shaft assembly 46 consists of a tunneling shaft or rod 47 formed of a suitable material such as stainless steel, of a suitable length, as for example 18 inches, and a suitable diameter of approximately ⅛ inch. The tunneling rod 47 is provided with proximal and distal extremities 48 and 49.

An introducer member 51 is slidably mounted on the tunneling shaft or rod 47 and is formed of a suitable material such as plastic. The introducer member 51 is substantially hollow as shown and is provided with a bore 52 through which the tunneling shaft 47 extends. The introducer member 51 is provided with a substantially hemispherical tip 53 to form a rounded protrusion or first obturator through which the rod 47 extends. The introducer member 51 has a length such that when it is introduced into the bore 34 of the introducer sleeve, it extends out of the distal extremity of the introducer sleeve 32, as shown particularly in FIG. 1. This diameter of the introducer member 51 is sized so that it can be slidably mounted in the bore 34. The other end of the introducer member 51 is provided with a chamfer 54.

A disk-type seal 43 having a central opening is provided in the section 36 in alignment with the bore 37, and is adapted to permit the introduction of the introducer member 51 therethrough.

The section 36 forms one part of a three-piece handle 56 of the laparoscopic apparatus 31 which is sized so that it is adapted to be grasped by the human hand. As can be seen particularly in FIG. 4, the handle 56 is generally rectangular in cross-section. The handle 56 is provided with an intermediate section 57 which has a bore 58 extending therethrough in registration with the bore 37 and has the same general diameter as the bore 37 so that the introducer member 51 can travel therethrough. The sections of the handle 56 can be characterized as having first, second and third sections, in which section 36 is the first section and intermediate section 57 is the second section. Latching means is provided for interconnecting the intermediate section 57 to the end section 36, and consists of a pair of oppositely disposed latches 61 pivotally mounted on the pins 62 in the intermediate section 57. Each of the latches 61 is provided with a latch portion 63 adapted to engage a protrusion 64 provided on the end section 36, and is yieldably urged into engagement therewith by a spring 66. Each of the latches is provided with a cam surface 67 which is adapted to be engaged by the chamfer 54 of the introducer member 51 to cam the latch portion 63 out of engagement with the protrusion 64 to release the intermediate section 57 from the end section 36 for a purpose hereinafter described.

The handle 56 also consists of another end section 71, which can also be characterized as the third section, which is secured to the proximal extremity of the tunneling shaft or rod 47. A pair of latches 72 are provided in the end section 71 and are pivotally mounted on pins 73. The latches 72 are provided with latch portions 74 adapted to engage projections 76 provided in the intermediate section 57. Means is provided for yieldably retaining the latches 72 in engagement with the projections 76 and consists of a U-shaped spring 77 mounted within the end section 71 and engaging the latches 72. The latches 72 are provided with knurled portions 72a which extend outwardly which are adapted to be grasped by the fingers of the hand so that the latch portions 74 can be moved out of engagement with the projections 76 against the force of the spring 77.

The tunneling shaft assembly 46 also includes a tunneling member or tip 79 which is mounted on the distal extremity of the tunneling shaft or rod 47. As shown, the tip 79 is substantially olive-shaped and can also be called a second obturator. It is provided with a rounded hemispherical surface on its distal extremity which has a maximum diameter which is slightly less than the diameter of the bores 34 and 37 so that it can pass through the introducer sleeve 32. The proximal extremity of the tip 79 is of smaller diameter to provide an annular step 81 in the tip. The proximal extremity of the tip 79 is also hemispherical, as shown. The tunneling member or tip 79 can be formed of a suitable material such as plastic and can be secured to the distal extremity of the tunneling shaft or rod 47 by suitable means such as an adhesive. As hereinafter explained, the tunneling shaft or rod 47 is movable so that the tip 79 can be brought into engagement with the hemispherical end 53 of the introducer member 51 for a purpose hereinafter described.

The laparoscopic apparatus 31 also includes a balloon assembly 86 which is shown in FIGS. 2, 5 and 6. As shown in FIG. 5, when the balloon assembly 86 consists of a balloon 87 which in plan, when deflated, has a pear-shaped configuration. The balloon is preferably formed of a non-elastomeric, medical-grade material of a suitable type such as PVC. Thus, the balloon 87 can be formed of two sheets 88 and 89 of such a material which have their outer margins bonded together by suitable means such as by a heat seal 91 extending around the perimeter of the flat balloon 87. The balloon 87 is provided with a neck 94 into which a flexible tubular member 96 extends, and is secured therein in a suitable airtight fashion such as by an adhesive. The tubular member 96 is provided with a lumen 97 which is in communication with the interior of the balloon and which can be used for inflating the balloon through a Luer-type fitting 98 mounted on the free end of the tubular member 96.

Means is provided for removably securing the balloon 87 to the tunneling rod or shaft 47, and consists of a sleeve 101 formed of the same material as the balloon 87, and which can be formed integral or separate therefrom and adhered thereto by suitable means such as an adhesive. The sleeve 101 extends longitudinally of the balloon 87 and is disposed generally equidistant from the side margins of the same. The sleeve 101 is provided with a passage 102 extending therethrough which is sized to slidably accommodate the tunneling shaft or rod 47. Means is provided for permitting separation of the balloon 87 from the tunneling rod by movement sidewise from the axis of the passage 102 and takes the form of longitudinally spaced apart perforations 103 in the sleeve 101 extending longitudinally the length of the sleeve 101. The perforations 103 are spaced close enough together to form a weakened region so that the balloon can be readily separated from the tunneling rod by separating the plastic sleeve 101 by tearing the plastic between the perforations as hereinafter described.

As shown in FIG. 6, the sleeve 101 is disposed equidistant from the side margins of the balloon, permitting the balloon to be inflated as hereinafter described and as also shown by the dotted lines in FIG. 6, to be inflated around the rod 47. When deflated, the side margins of the balloon 87 can be rolled inwardly toward the rod 47 as shown by the broken lines in FIG. 6 to permit the same to be folded into a generally cylindrical configuration as shown in FIG. 2, and to be enclosed within a removable sleeve 106 carried by the tunneling shaft or rod 47. The removable sleeve 106 is formed of a relatively thin-walled tubular member 107 of a suitable material such as Teflon which has a weakened region 108 in its wall extending longitudinally the length thereof. This weakened region 108 can take the form of a slit as shown, or can be a series of perforations or slots formed in the wall, or a combination thereof. The proximal extremity of the tubular member 107 is provided with split-apart or separable end portions 107a and 107b to which are secured finger rings 109 of a suitable material such as plastic and secured thereto by fasteners 111.

Operation and use of the laparoscopic apparatus in performing the method for laparoscopic hernia repair through preperitoneal space may now be briefly described as follows. Let it be assumed that the laparoscopic apparatus 31 has been assembled as shown in FIG. 1. As shown in FIG. 7, let it be assumed that a human patient 121 is in a prone position and has a hernia 122 in the lower abdominal area which he wishes to have repaired. The patient is prepared in an appropriate manner by administering a suitable anesthesia, as for example a spinal anesthesia, and any other necessary preparation. The surgeon first makes an infraumbilical incision 126 in the skin below the navel or umbilicus 127 and separates the fat 129 and then incises the anterior rectus sheath or fascia 131 in the midline. Care should be taken not to penetrate the peritoneum overlying the abdominal cavity 133 (see FIG. 8).

After the incision 126 has been made in the manner hereinbefore described, the laparoscopic apparatus 31 is then taken by one hand of the surgeon, grasping the handle 56 and utilizing the other hand to facilitate the insertion of the rounded blunt tip 79 into the incision 126. The blunt tip 79 is caused to enter the slit in the fascia 131 and pass anterior to the peritoneum 132, in between the rectus muscles (laterally), and enters the potential preperitoneal space 136 to be provided for the laparoscopic procedure. The blunt tip 79 is then utilized as a tunneling device by the surgeon using one hand 56 to advance the blunt end 79 toward the pubic region of the patient while the surgeon places his other hand on the abdomen to feel the apparatus or device 31 as it is being advanced. The advance of the device 31 is continued until the blunt tip 79 is below the symphysis pubis 137 as shown in FIG. 8, and preferably is disposed between the symphysis pubis 137 and the bladder 138.

After the apparatus or device 31 has been properly positioned as shown in FIG. 8, the removable sleeve or sheath 106 is removed by the surgeon using one hand to engage the finger rings 109 which are exterior of the body of the patient and outside of the incision 126. At the same time, the other hand of the surgeon is utilized to stabilize the portion of the device 31 which is within the preperitoneal space. The sheath 106 can be readily withdrawn since it is formed of Teflon and is split or weakened along its length, by pulling it proximally and away from the longitudinal axis of the tubular member 33. As the sheath 106 opens and slips off, it exposes the balloon 87 of the balloon assembly 86. When the sheath 106 is completely removed, a sterile saline solution serving as a balloon inflation medium is introduced into the balloon 87 through the tubular member 96 by connecting a conventional syringe 141 to the Luer fitting 98. The balloon 87 typically can be inflated to a suitable size by introducing 500 cc or less of normal saline solution into the balloon by pressing on the plunger 142. As the balloon 87 is inflated, the balloon progressively unwraps with its side margins rolling outwardly from the center while expanding into a plane to cause progressive separation or dissection of tissue (i.e. 131, 132) along its weakest points by application of forces generally perpendicular to the plane of the balloon as indicated by the arrows 143 in FIGS. 6 and 9, to create the preperitoneal or anatomic space. The balloon 87 expands around the tunneling shaft 47 in the manner shown in broken lines in FIG. 6 to achieve the progressive separation until complete inflation is achieved. The surgeon can sense the filling of the balloon by feeling the abdomen of the patient as the balloon is inflated. The balloon 87 serves to open up the preperitoneal space 136 to provide a bloodless space for the procedures hereinafter to be performed. Since the balloon is formed of a non-elastomeric material, it is a volume-limited balloon to prevent overexpansion. Different sizes of balloons can be utilized for different patient sizes. With a smaller balloon it is possible to deflate the balloon and then shift the balloon and again reinflate it to obtain the desired bloodless preperitoneal space.

After the desired bloodless anatomic space or pocket 136 is formed, the balloon 87 is deflated by withdrawing the normal saline solution by withdrawal of the plunger 142 of the syringe 141 or via a hospital vacuum aspirator. After the balloon 87 has been deflated, the balloon assembly 86 can be removed by grasping the handle 56 of the laparoscopic apparatus or device 31 with one hand and using the other hand to grasp the tubular member 96 and the proximal extremity of the balloon 87 and to remove the same through the incision 126, as shown in FIG. 10. As the balloon 87 is being removed, it is progressively separated from the tunneling rod or shaft 47 by causing the sleeve 101 to split apart along the longitudinal perforations 103 provided in the sleeve 101. This makes it possible to separate the balloon 87 from the tunneling rod 47 without the necessity of removing the tunneling rod 47 or the introducer device 32.

Figure 11:
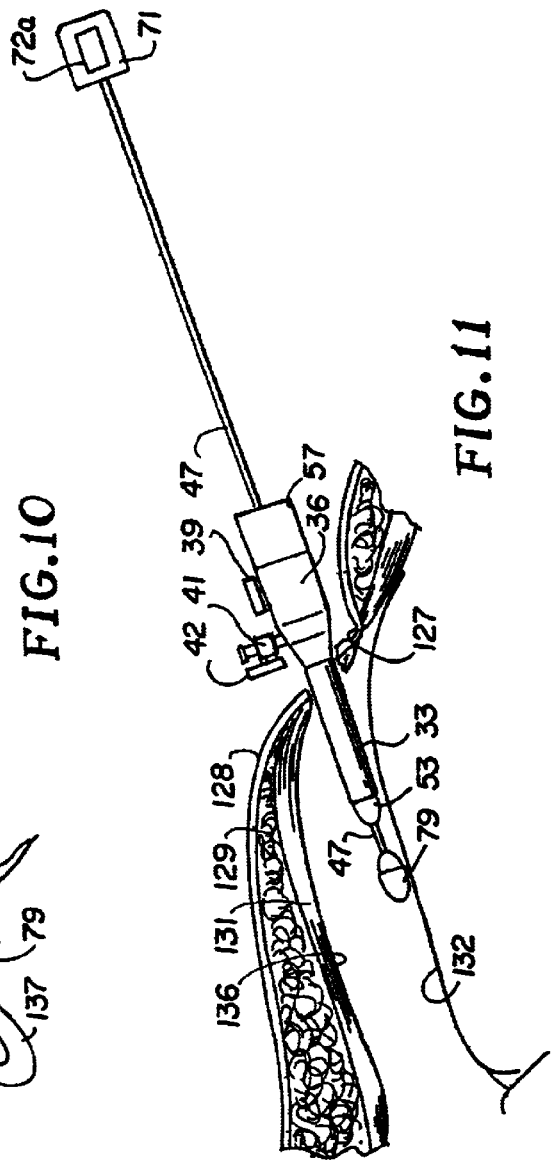
FIG. 11 is a sagittal view similar to FIG. 8 showing removal of the tunnelling shaft.

After the balloon assembly 86 has been removed, the introducer device 32 can be advanced distally over the tunneling shaft or rod 47 so it extends well into the preperitoneal space 36 as shown in FIG. 11. The end section 71 of the handle 56 is then removed by depressing the latches 72 by having the fingers engage the portions 72a to disengage the latch portions 74 from the intermediate section 57 of the handle 56. The end section 71 is then drawn proximally as shown in FIG. 11 to bring the olive-shaped tip 79 into engagement with the obturator 53 disposed in the distal extremity of the tubular member 33 to cause both the tip 79 and the obturator 53 to be withdrawn or retracted. As the introducer member 51 is being withdrawn, its chamfer 54 will strike the cam surfaces 67 of the latches 61 to cause them to disengage from the end piece 36 to carry it along with the introducer member 51 and shown in FIG. 2. Thus, it can be seen that the tunneling shaft assembly 46 can be readily removed merely by one motion of the surgeon's hand. Thereafter, a conventional laparoscope 144 (see FIG. 16) can be introduced through the introducer sleeve 32 to permit the surgeon to view the preperitoneal space 136.

The dissected preperitoneal space 136 is then insufflated with carbon dioxide through the stopcock 41 to a pressure ranging from 6 to 8 mm of mercury. Thereafter, two additional trocars 146 and 147 are introduced through the abdominal wall into the dissected preperitoneal space 136 in appropriate locations. Thus, as shown in FIG. 7, trocar 146 is introduced into the left side of the abdomen of the patient below the introducer sleeve 32 and the trocar 147 is introduced into the dissected preperitoneal space immediately above the symphysis pubis and directly below the introducer sleeve 32. As can be appreciated, the locations of the trocars 146 and 147 is generally dictated by the location of the hernia 122 to be repaired.

A patch 151 of the present invention to be utilized in the hernia repair procedure is shown in detail in FIGS. 12, 13 and 14. The patch 151 can be characterized as a hernia patch or graft and is made of a suitable plastic mesh such as a Prolene mesh manufactured by Ethicon, Inc. The patch 151 can be of any desired configuration. For example it can be generally circular as shown, and consists of a disk 152 of a suitable diameter, as for example 2 inches. A tail 153 is secured to the disk substantially in the center thereof, in a suitable manner. For example, as shown, the tail 153 can be provided with split portions 153a and 153b which are split apart and offset with respect to each other, which are secured to a smaller reinforcing disk 154 formed of the same material as disk 152 and secured to the disk 152 by suitable means such as surgical thread (not shown). The tail 153 is formed of the same material as the disk 152 and 154, or it can be formed of a different material, such as Goretex. It can have a size such that it has a width of approximately ½ inch and a length of approximately 1½ inches. As shown particularly in FIG. 14, the side margins of the disk 152 can be rolled inwardly towards the center adjacent the tail 153 to form a cylindrical roll 156 such as shown in FIG. 14 with the tail 153 extending outwardly therefrom. The roll 156 can be maintained in its rolled-up condition by means of sutures 157 disposed adjacent opposite ends of the roll and on opposite sides of the tail 153.

Conventional laparoscopic instruments are utilized which are introduced through the trocars 146 and 147 while visualizing the same through the laparoscope 144 introduced through the introducer device 32 to dissect the hernia 161 to permit visualization of its neck 162 as it is entering the internal inguinal ring 163. The hernia sac 161 is dissected from the surrounding tissue (spermatic duct and vessels) (see FIG. 15). The process is facilitated by $CO_2$ pressure impinging on the neck of the hernia sac. As soon as this dissection is completed, the roll 156 is pushed into the trocar 147 and advanced through the same by suitable means such as a deployment rod 164 (see FIG. 16) to enter the dissected preperitoneal space 13 as shown in FIG. 16. Alternatively, the roll 156 can be placed in a tubular member (not shown) which can be used to position the roll 156 within the trocar 157. Thereafter, by the deployment rod 164, the roll 156 can be pushed out of the tubular member into the dissected preperitoneal space 136.

Figure 17:
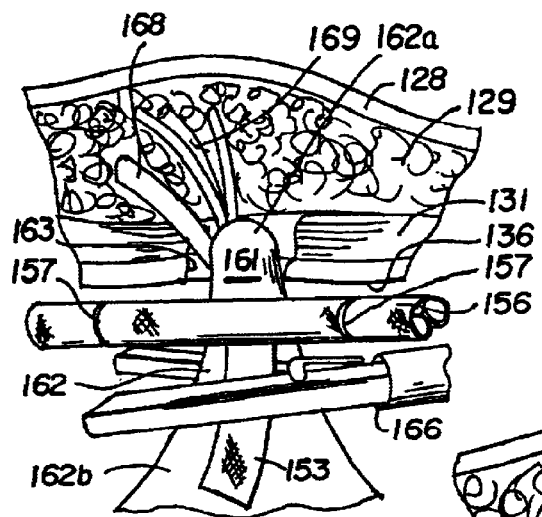
FIG. 17 is a sagittal view similar to FIG. 16 showing the attachment of the patch to the hernia sac.
Figure 18:
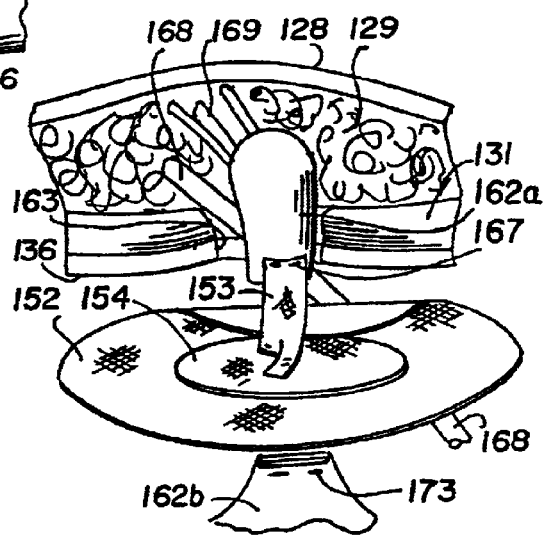
FIG. 18 is a sagittal view similar td FIG. 17 showing the dissection of the hernia sac and the unrolling of the patch.
Figure 19:
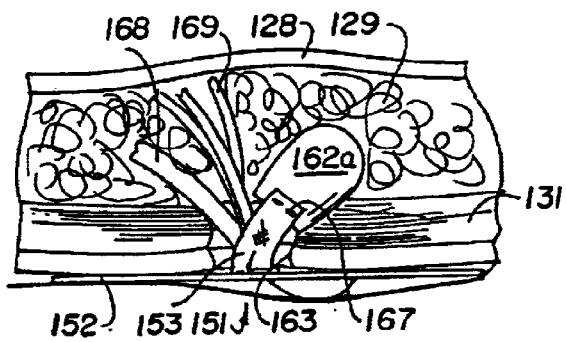
FIG. 19 is a sagittal view showing the patch in place to provide the hernia repair.

The roll 156 after it is in the preperitoneal space is then manipulated so that its tail 153 is disposed alongside the neck 162 of the hernia sac 161 as shown in FIG. 17. A conventional stapling device 166 is then introduced through the trocar 146 to staple the tail 153 to the neck 162 by placing staples 167 therein. These staples 167 serve to divide the neck of the sac into distal and proximal portions 162a and 162b. As soon as this stapling operation is completed, the two portions 162a and 162b are separated from each other because of the pressure of the insufflation gas to cause the tail 153 of the patch 151 to be pulled upwardly into the inguinal ring to pull with it the disk 152. The sutures 157 are cut apart to permit the disk 152 to unroll and to be placed across the inguinal ring 163 which created the main weakness in the abdominal wall permitting the hernia which is being repaired to occur. The proximal portion 162b of the neck 162 is stapled together by staples 173 as shown in FIG. 18. The proximal portion 162 is then permitted to fold back into the desired anatomical location within the abdomen.

Thereafter, while observing the procedure under the laparoscope, the dissected preperitoneal space 136 can be deflated by permitting the carbon dioxide gas to escape to the atmosphere through the stopcock 41 in the introducer device 32 by operation of the stopcock lever arm 42. As deflation is taking place, the movement of the patch 151 is observed through the laparoscope 144 so that it does not become misplaced. When the deflation has been completed, the patch 151 is in a position over the inguinal ring 163 and serves to provide enforcement to prevent the occurrence of another hernia in that area. The tail 153 is disposed with the inguinal ring 163 and retains the mesh disk 152 so that it surrounds the inguinal ring 163.

After deflation has been accomplished, the trocars 146 and 147 as well as the introducer device 32 can be removed. Small sutures can then be utilized to close the various small openings which have been provided in the abdominal wall so that upon healing there will be minimal noticeable scars from the procedure. The scar in the navel or umbilicus typically is almost nearly invisible.

It has been found that the use-of the laparoscopic apparatus 31 in accomplishing the method as hereinbefore set forth provides a procedure in which the pain after the operation is markedly reduced. This is particularly true since the operation does not involve suturing of any ligaments which typically produces the pain. In addition, the recovery time for the patient is greatly accelerated. In the procedure of the present invention, a patient can return to work within a matter of 3 to 5 days rather than in a number of weeks as in a conventional hernia repair procedure. The procedure also has other advantages. For example, there is a lack of necessity for a general anesthesia. Another principal advantage of the procedure is there is no contact of mesh patch 151 with the intestines of the patient or other intra-abdominal structures, thus greatly reducing the possibility of adhesion formation. In addition, the graft which is formed by the patch 151 is more secure and is positioned in an anatomically correct position. This is because the hernia sac is in exact alignment with the hernia and pulls with it the tail 153 of the graft to ensure that the graft formed by the patch 151 is drawn into the correct position and is maintained in that position to prevent migration. In addition, the graft, by having an additional central disk 154, ensures that additional reinforcement is provided in the proper location in the center where the weakest region in the abdominal wall has occurred. In addition, by such proper centering, the mesh construction of the patch 151 serves to uniformly reinforce the area surrounding the hernia.

Figure 20:
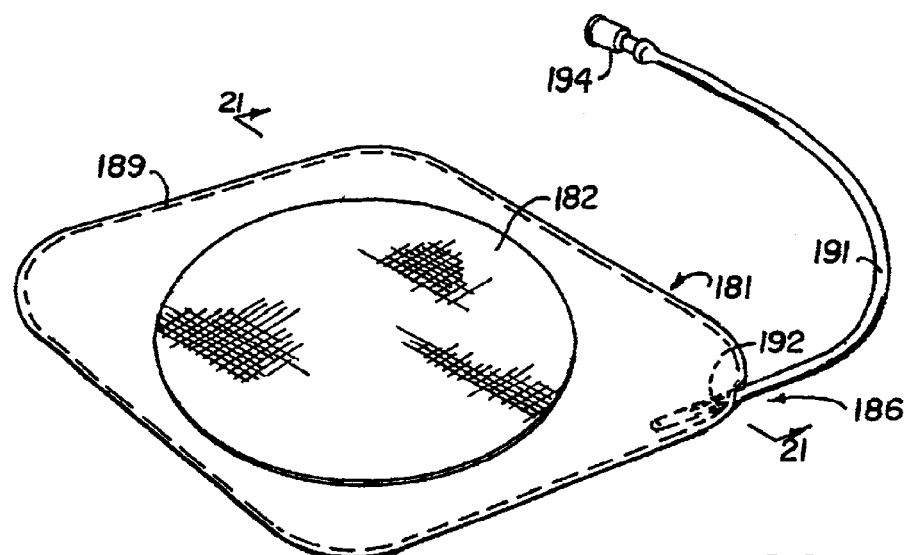
FIG. 20 is an isometric view of another embodiment of a balloon with a patch disposed thereon for use with the apparatus of the present invention.
Figure 21:
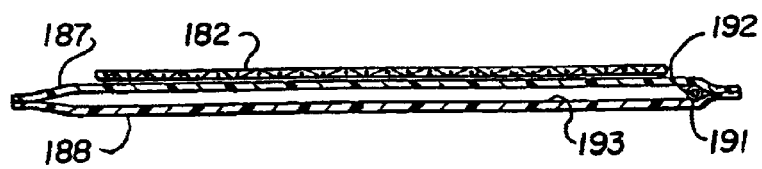
FIG. 21 is a cross-sectional view taken along the line 21—21 of FIG. 20.
Figure 22:
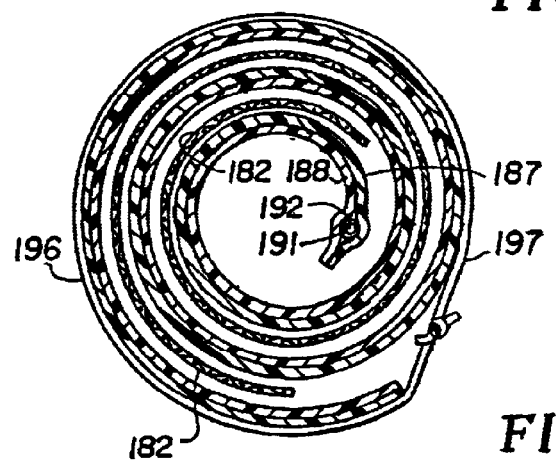
FIG. 22 is an enlarged cross-sectional view taken along the line 22—22 of FIG. 23.

Another embodiment of the present invention is shown in FIGS. 20, 21 and 22 with respect to another embodiment of a balloon assembly 181 and another embodiment of a patch or graft 182. The balloon assembly 181 consists of a balloon 186 formed of two sheets 187 and 188 which are rectangular in shape, as for example square as shown in FIG. 20, which are heat-sealed together at their outer margins as indicated by the broken line 189. A tubular member 191 is provided which has one end sealed into one corner of the balloon 186 as shown in FIG. 20. The tubular member 191 is provided with a lumen 192 which opens up into the interior space 193 of the balloon. The sheets 187, 188 are formed of a non-elastomeric material of the type hereinbefore described. A Luer fitting 194 is connected into the free end of the tubular member 191 and is utilized for introducing a saline solution into the balloon 186 for inflating the same.

The graft or patch 182 can have a desired configuration, as for example circular as shown in FIG. 20. It is formed of a non-absorbable synthetic surgical mesh, as for example from polypropylene manufactured by Ethicon Inc. As shown, the mesh patch 182 overlies the sheet 187.

Figure 23:
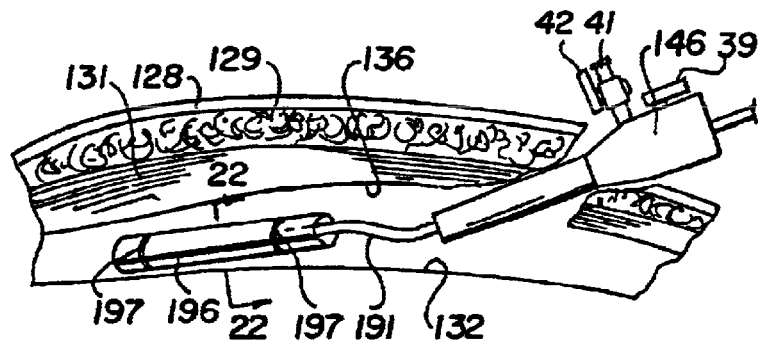
FIG. 23 is a sagittal view showing the manner in which the balloon and patch shown in FIG. 20 are disposed in the preperitoneal space.
Figure 24:
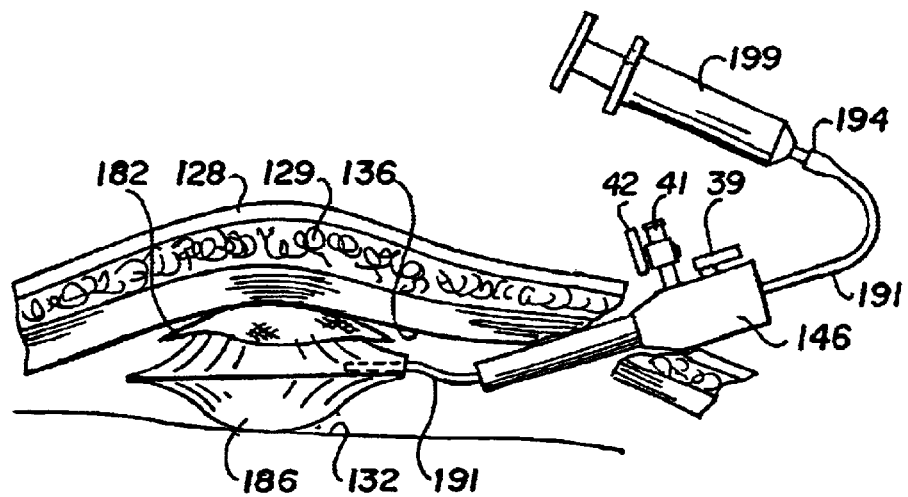
FIG. 24 is a sagittal view showing the placement of the balloon and the patch of FIG. 20, and the inflation of the balloon in the preperitoneal space.

The balloon assembly 182 with the patch 182 thereon can be rolled up into a roll 196 as shown in FIG. 22 in which the patch or graft 182 is disposed within the roll. The roll can be maintained in the roll configuration by sutures 197 wrapped about the same. The roll 196 can then be introduced through a side trocar 146 and introduced into the dissected preperitoneal space 136 with the tubular member 191 extending through the trocar 146 and having its Luer fitting 194 disposed outside of the trocar. After the roll 196 has been introduced, the sutures 197 can be removed and the balloon can be inflated by introducing a saline solution through the fitting 194 by use of a syringe 199. Before the saline solution is introduced to inflate the balloon, the roll 196 is properly positioned so that when it is inflated and begins to unroll it will unroll in the proper direction so that the graft or patch 182 carried thereby is properly positioned as shown in FIG. 23. After the roll 196 has been completely unrolled, continued inflation of the balloon 186 moves the patch 182 so that it is pressed against the portion of the fascia through which the hernia has occurred as shown in FIG. 24. As soon as the graft 182 has been properly positioned, the balloon 186 is deflated. The trocar 146 is then removed, and thereafter the balloon can be withdrawn through the opening in which the trocar was present. Thereafter, the gas utilized for insufflation can be permitted to discharge through another trocar so that the fascia 131 comes into engagement with the peritoneum 132 with the large-area patch 182 held in place therebetween. Thereafter, the trocars can be removed in the manner hereinbefore described to complete the procedure.

Another embodiment of a balloon assembly for deploying a large-area patch or graft through a trocar is shown in FIG. 25. The large-area graft 201 shown in FIG. 25 is formed of a mesh material of the type hereinbefore described and has a generally oval-shaped configuration conforming to the general shape of the balloon 202 of the balloon assembly 203. The balloon 202 is constructed of a non-elastomeric material in the manner hereinbefore described. A tubular member 206 is provided for inflating the balloon and has a Luer fitting 207 on the free end thereof. Means is provided for retaining the mesh graft 201 on one side of the balloon and consists of plastic flaps 208 provided on opposite sides of the balloon 202, and secured thereto by a suitable means such as a heat seal along the broken line 209. The inner margins of the flaps 208 are free and are adapted to receive the outer margins of the graft 201 as shown particularly in FIG. 25.

The balloon 202 with the mesh graft 201 thereon can be rolled up into a substantially cylindrical roll 211 by rolling the outer margins of the balloon inwardly on top of the mesh material to provide two rolls 211 and 212 which are brought in adjacent to each other as shown in FIG. 26 with the mesh graft 201 being wrapped up therewith. The two rolls 211 and 212 can then be inserted into a tubular sheath 214. The sheath 214 can then be introduced through a trocar in a manner hereinbefore described and then pushed out of the sheath into the abdominal cavity. The balloon can then be inflated with a saline solution to cause the two rolls 211 and 212 to unroll in opposite directions and then for the balloon to inflate to-move the patch 201 carried thereby into engagement with the portion of the fascia having the hernia therein. Thereafter, the balloon can be deflated, the trocar removed, the balloon removed, and the dissected preperitoneal space deflated so that the large mesh graft 201 is disposed between the fascia and the peritoneum and is retained in position therebetween.

Another embodiment of a graft which can be utilized in connection with the present invention is shown in FIG. 27. The patch or graft 216 is constructed in a manner similar to the graft or patch 151 shown in FIGS. 12 and 13, with the exception that it is constructed in a manner so that it can be utilized with a direct hernia rather than an indirect inguinal hernia hereinbefore described. The graft 216 is formed of a sheet of circular mesh in the form of a disk 217 with a reinforcing central disk 218 which has a barbed head 219 secured thereto. The barbed head 219 is formed of a biodegradable material such as polyglycolic acid. The mesh graft 216 can be folded over a deployment rod 221 and introduced into a cylindrical sheath 222 (see FIG. 28) which is sized so that it can be introduced through a conventional trocar, then deployed from the sheath 22 by pushing on the deployment rod 221. After the graft 216 has been deployed into the dissected preperitoneal space 136, it can be positioned in an appropriate manner so that the barb 219 is positioned so that it is in alignment with the inguinal ring whereby upon deflation of the preperitoneal space 136, the barb 219 will extend through the inguinal ring to serve to retain the graft 201 firmly in place.

Another embodiment of a laparoscopic apparatus incorporating the present invention is laparoscopic apparatus 231 as shown in FIGS. 29 through 32. The laparoscopic apparatus 231 includes introducer sleeve or device 32 identical to that hereinbefore described. It also includes a tunneling shaft assembly 46 which is provided with a tunneling shaft or rod 47 and a proximal extremity 49 (see FIG. 32). In the previous embodiment of the laparoscopic apparatus, the tunneling shaft assembly is provided with an olive-shaped or bullet-shaped tip 79 which was secured to the distal extremity 49 of the tunneling shaft 47. In the present embodiment of the apparatus shown in FIGS. 29 through 32, the obturator tip 79a is detachably mounted on the distal extremity 49 of the tunneling rod 47. The proximal extremity of the tip 79a is provided with a slot 236 which extends through one side of the proximal extremity into the central portion of the proximal extremity of the tip 79a. The slot 236 is adapted to receive the rounded extremity 237 provided on the distal extremity 49 of the tunneling rod 47 (see FIG. 32). A removable sleeve 241 is provided as a part of a laparoscopic apparatus 231, and is similar in many respects to the removable sleeve or sheath 106 hereinbefore described. The removable sleeve 241 is formed of a suitable material such as Teflon as hereinbefore described and is provided with a tubular member 242 which is provided with a relatively thin wall 243 that has a weakened portion extending longitudinally thereof in the form of a slit 244 (see FIG. 31). The tubular member 242 is provided with a proximal extremity 246 and a distal extremity 247. The proximal extremity 246 has a thicker cross-section than the distal extremity 247, as shown in FIGS. 31 and 32. The proximal extremity 246 is provided with a recess 248 formed in the wall which is diametrically opposite the slit 244 that serves as a relief region to permit the movable sleeve 241 to be split apart when it is removed from the balloon.

The proximal extremity 246 is provided with wing-like members 251 and 252 which extend diametrically therefrom, spaced 90° apart from the slit 244. These outstretched wings 251 and 252 serve to help the physician orient the laparoscopic apparatus 231 as it is being utilized. The proximal extremity 246 is also provided with a handle 256 which is formed integral therewith and which extends radially from the tubular member 242. The handle 256 is provided with a finger hole 257 extending therethrough through which a finger can be inserted to facilitate pulling the removable sleeve 241 off of the balloon as described in connection with the previous embodiment.

Figure 33:
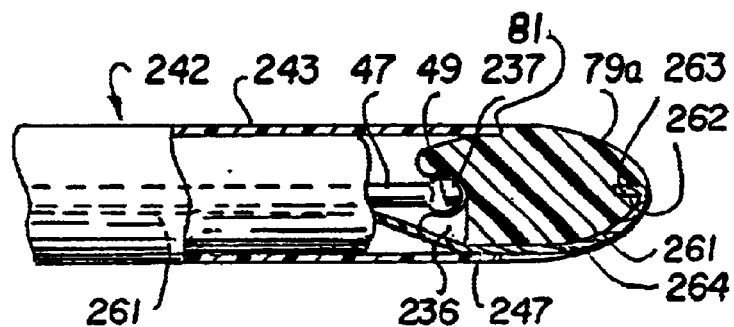
FIG. 33 is an enlarged cross-sectional view of the distal extremity of the laparoscopic apparatus shown in FIG. 29.
Figure 34:
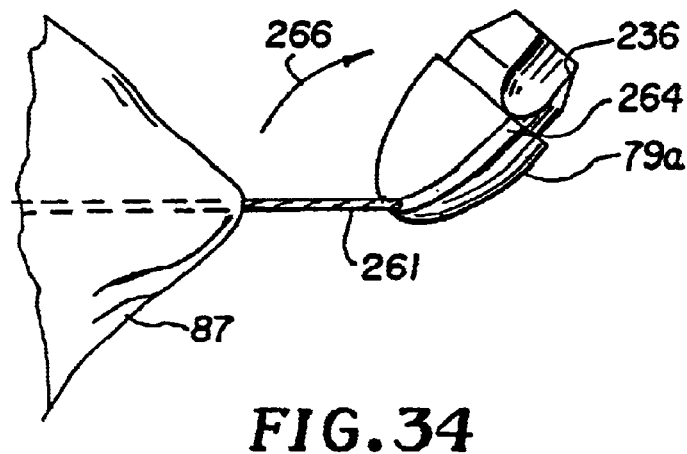
FIG. 34 is a partial plan view showing the balloon after it has been removed from the laparoscopic apparatus with the obturator tip shifting its position.
Figure 35:
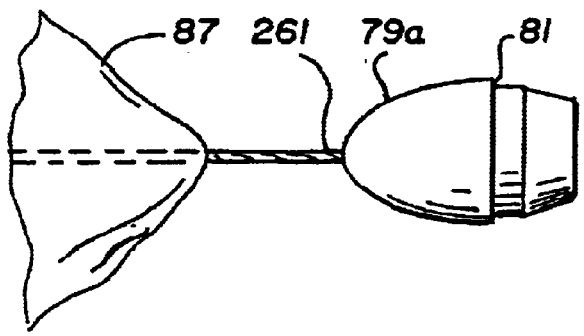
FIG. 35 is a plan view of the balloon shown in FIG. 34 as it is being removed from the body of the patient and bringing along with it the obturator tip.

As shown in FIG. 33, the tip 79a is detachably mounted in the proximal extremity of the removable sleeve 241 so that the tip 79 can serve as a second obturator during introduction of the laparoscopic apparatus 231 as hereinbefore described. Means is provided for securing the detachable tip 79a to prevent it from becoming separated from the laparoscopic apparatus 231 and for permitting its withdrawal after the laparoscopic procedure is being completed. As shown in FIGS. 33 and 34, such means consists of a flexible elongate element 261 in the form of a braided string formed of a suitable fabric such as Nylon, which has one end 262 secured in a slot 263 provided on the distal extremity of the tip 79a by suitable means such as an adhesive (not shown). The flexible elongate element 261 extends from the distal extremity of the tip 79a in a recess 264 opening through the external surfaces of the tip 79a. The proximal extremity of the flexible elongate element 261 can be secured directly to the balloon 87 or, alternatively, it can extend through the perforated sleeve 101 provided in the balloon along the tunneling shaft so that it extends beyond the proximal extremity of the tunneling shaft.

The use of the laparoscopic apparatus 231 in performing a laparoscopic procedure is substantially identical to that hereinbefore described with the exception that when the removable sleeve 241 is removed from the balloon 87, the removable sleeve can be pushed forwardly to detach the tip 79a from the tunneling shaft 47. The removable sleeve 241 then can be pulled rearwardly to separate it from the balloon along the slit 244. As soon as this occurs, the tip 79 becomes free of the sleeve and begins to rotate in the direction of the arrow 266 shown in FIG. 34. When the balloon has been inflated and has performed its functions as hereinbefore described and it is now desired to remove the balloon 87, the balloon 87 can be withdrawn in the manner hereinbefore described, and since the tip 79a is tethered to the balloon 87 itself or flexible elongate element 261 attached thereto extends out proximally of the balloon 87, the tip 79a is withdrawn or can be withdrawn with the balloon 87.

This laparoscopic apparatus 231 with its detachable obturator tip 79a will be useful in certain applications of the present invention. With the previous laparoscopic apparatus hereinbefore described, there is a possibility that when the obturator tip 79 is withdrawn, critical structures, as for example small arteries, may be inadvertently incised between the tip 79 and the distal extremity of the tubular member 33 of the introducer device 32. This possibility is eliminated by having the detachable tip 79a, which is withdrawn when the balloon is withdrawn.

Still another embodiment of the laparoscopic apparatus incorporating the present invention is shown in FIGS. 36, 37 and 38, in which the laparoscopic apparatus 271 consists of a balloon 272 of the type hereinbefore described, which is provided with a perforated sleeve 273 through which the tunneling rod 47 extends. The distal extremity 274 of the sleeve is closed by an end piece 276. The balloon 272 is wrapped in the manner hereinbefore described around the tunneling shaft 247. The tunneling shaft or rod 47 is not provided with a tunneling member or second obturator of the type hereinbefore described but its end is rounded as shown by providing a rounded tip 47a.

The wrapped balloon 272 is enclosed within a removable sleeve 281 which is similar to those hereinbefore described. It is provided with a tubular member 282 that has a weakened region in the form of a slit 283 extending longitudinally the length thereof. The removable sleeve 281 differs from those hereinbefore described in that rather than being open at the end as in previous embodiments, it is provided with a closed-end, bullet-shaped or olive-shaped tip 286. The slit 283 is provided with a curved portion 283a which extends through the bullet-shaped tip 286 so that the sleeve can be peeled off of the balloon 272 in the manner hereinbefore described by pulling on the handle 288 having a finger hole 289 therein. During the time that the removable sleeve 281 is being peeled off or separated from the balloon 272, the balloon is held in place by the tunneling rod 47 which engages the end 276 of the perforated sleeve 273. The balloon 272 after it is inflated can be separated from the tunneling rod 47 by pulling on the balloon and causing its distal extremity to lift up and to break apart at the perforations and peel away from the rounded extremities 47a of the tunneling shaft 47 as shown in FIG. 38. Continued pulling on the balloon 272 will cause it to separate from the tunneling rod 47 so that the balloon 272 can be removed as hereinbefore described. Thus, it can be seen that there has been provided an embodiment of the laparoscopic apparatus of the present invention in which the need for an obturator carried by the distal extremity of the tunneling rod 47 has been eliminated by providing the second obturator as a part of the removable sleeve 281. In all other respects, the operation and use of the laparoscopic apparatus 271 is similar to that hereinbefore described.

From the foregoing it can be seen that there has been provided an apparatus and method for developing an anatomic space by the use of a wrapped balloon which, as it is inflated, gradually unwraps to tend to form a plane to cause forces to be created perpendicular to the plane for pulling apart tissue along a natural plane to provide an anatomic space, thereby providing a dissection in the weakest plane creating a more natural, less traumatic and bloodless region in which to perform various medical procedures. Such anatomic spaces can be created in various parts of the human body, for example in the preperitoneal area to provide a space anterior to the peritoneum for hernia repair and for varocele dissection. Spaces can also be developed lateral to the peritoneum and spaces posterior to the peritoneum for performing medical procedures such as a sympathectomy and a lymph node dissection.

As hereinbefore explained, the apparatus and method is particularly appropriate for performing laparoscopic hernia repair, permitting the use of grafts and patches which can be used for direct and indirect hernias with minimal pain to the patient and with the patient being able to return to work within a few days.

What is claimed is:

1. In a method for laparoscopic hernia repair through the preperitoneal space of a patient having an abdominal area with overlying tissue and a peritoneum with a preperitoneal area being disposed between the overlying tissue and the peritoneum using laparoscopic apparatus having an introducer device with a tubular member having a bore therein, a tunneling assembly disposed in the bore and a balloon wrapped about a tunneling shaft and a removable sleeve enclosing the balloon, the method comprising the steps of making an incision in the abdominal area, introducing the laparoscopic apparatus into the incision so that the tubular member of the introducer device is disposed in the preperitoneal area, advancing the tunneling shaft with the balloon thereon to separate the overlying tissue from the peritoneum, removing the sleeve to expose the balloon, inflating the balloon with a balloon inflating medium to create a dissected preperitoneal space between the peritoneum and the overlying tissue, deflating the balloon, removing the balloon, insufflating the dissected preperitoneal space with a gas, introducing a graft into the dissected preperitoneal space, positioning the graft in the desired location, and deflating the preperitoneal space to permit the graft to come into contact with tissue overlying the peritoneum, removing the introducer device and closing the incision.

2. A method as in claim 1 together with the step of introducing the graft into the dissected preperitoneal space with an additional balloon as the additional balloon is introduced in the dissected preperitoneal space.

3. A method as in claim 2 together with the step of forming the additional balloon and the graft into at least one roll and wherein the additional balloon and the graft are introduced into the dissected preperitoneal space as a roll.

4. A method as in claim 3 together with the step of causing the additional balloon to unroll in a single direction as it is inflated.

5. A method as in claim 3 wherein the additional balloon is unrolled in first and second directions as the additional balloon is inflated.

* * * * *